United States Patent [19]
Gompper et al.

[11] Patent Number: 5,948,551
[45] Date of Patent: *Sep. 7, 1999

[54] USE OF CONJUGATED COMPOUNDS CONTAINING PYRIMIDINE GROUPS AS ELECTROLUMINESCENCE MATERIALS

[75] Inventors: Rudolf Gompper, München; Stefan Brandl, Riemerling; Hans-Jürgen Mair, Friedberg, all of Germany

[73] Assignee: Hoechst Aktiengesellschaft, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/496,596

[22] Filed: Jun. 29, 1995

[30] Foreign Application Priority Data

Jul. 1, 1994 [DE] Germany .................. 4423098

[51] Int. Cl.$^6$ .................. H05B 33/14; C07D 403/00
[52] U.S. Cl. .................. 428/690; 428/411.1; 428/917; 313/504; 313/506; 252/301.16; 544/242; 544/296
[58] Field of Search .................. 428/690, 917, 428/411.1; 313/504, 506; 252/301.16, 301.25; 544/242, 294, 296, 333

[56] References Cited

U.S. PATENT DOCUMENTS

| | | |
|---|---|---|
| 3,239,406 | 3/1966 | Coffman et al. . |
| 3,658,817 | 4/1972 | Orlando . |
| 3,660,404 | 5/1972 | Otterstedt et al. . |
| 3,787,428 | 1/1974 | Otterstedt et al. . |
| 4,539,507 | 9/1985 | VanSlyke et al. .................. 313/504 |
| 4,609,485 | 9/1986 | Kitano et al. .................. 252/299.61 |
| 5,077,142 | 12/1991 | Sakon et al. .................. 428/690 |
| 5,346,772 | 9/1994 | Akiyama et al. .................. 428/457 |

FOREIGN PATENT DOCUMENTS

| | | |
|---|---|---|
| 160790 | 11/1985 | European Pat. Off. . |
| 186045 | 7/1986 | European Pat. Off. . |
| 213841 | 3/1987 | European Pat. Off. . |
| 225195 | 6/1987 | European Pat. Off. . |
| 237007 | 9/1987 | European Pat. Off. . |
| 260077 | 3/1988 | European Pat. Off. . |
| 301511 | 2/1989 | European Pat. Off. . |
| 311329 | 4/1989 | European Pat. Off. . |
| 322708 | 7/1989 | European Pat. Off. . |
| 339414 | 11/1989 | European Pat. Off. . |
| 351782 | 1/1990 | European Pat. Off. . |
| 0373582 | 6/1990 | European Pat. Off. . |
| 0387715 | 9/1990 | European Pat. Off. . |
| 409634 | 1/1991 | European Pat. Off. . |
| 3411571 | 10/1985 | Germany . |
| 3515373 | 11/1986 | Germany . |
| 3518734 | 11/1986 | Germany . |
| 3632411 | 4/1988 | Germany . |
| 3731619 | 4/1988 | Germany . |
| 3719424 | 12/1988 | Germany . |
| 44 09 431 | 10/1994 | Germany . |
| 60-25973 | 2/1985 | Japan . |
| 60-172971 | 9/1985 | Japan . |
| 61-33177 | 2/1986 | Japan . |
| 62-174047 | 7/1987 | Japan . |
| 63-57553 | 3/1988 | Japan . |
| 0131740 | 2/1989 | Japan . |
| 01104031 | 4/1989 | Japan . |
| 01113347 | 5/1989 | Japan . |
| 01135745 | 5/1989 | Japan . |
| 01290664 | 11/1989 | Japan . |
| 02142751 | 5/1990 | Japan . |
| 0356454 | 3/1991 | Japan . |
| 2193209 | 2/1988 | United Kingdom . |
| WO 87 05291 | 9/1987 | WIPO . |
| WO 87 07890 | 12/1987 | WIPO . |
| WO 88 08441 | 11/1988 | WIPO . |
| WO 90/13148 | 11/1990 | WIPO . |
| WO 93/06192 | 4/1993 | WIPO . |

OTHER PUBLICATIONS

T. Kanbara et al., "Preparation and Properties of Highly Electron–Accepting Poly(pyrimidine–2, 5–diyl)", *Chemistry Letters*, No. 4 (1992), pp. 583–586.

Angewandte Chemie, vol. 93, No. 3, 1981, pp. 298–299, XP002000760 by R. Gompper et al. entitled "Aminopyridine, Aminopyrimidine . . . ".

Tetrahedron, vol. 49, No. 45, 1993, pp. 10205–10218, XP002000761 by J.T. Gupton et al. entitled "The Preparation and Some Reactions . . . ".

Journal of Heterocyclic Chemistry, vol. 28, No. 5, 1991, pp. 1281–1285, XP000563722 by J.T. Gupton et al. entitled "An Alternative Preparation of the . . . ".

Winstel, G., "Electroluminescent Materials and Devices", in W. Gerhartz (ed).: *Ullmann's Encyclopedia of Industrial Chemistry*, vol. A9, 5th Ed. VCH Verlag 1987, pp. 255–264.

Kauffmann, T., et al., "Protophanes and Polyaromatics", *Chemical Abstracts* 83(23):193266m.

Otterstedt, J.–E., et al., *J. Heterocycl. Chem.* 9(1972) 2, 225–230, abstract only.

Mamaev, V.P., et al., "Synthesis of 2,5'–Bipyrimidines (VI), (VIII) from Substituted 5–Cyanopyrimidines (I)", *Khim. Geterotsikl. Soedin.* 1988, 3, 371–375, abstract only.

Yoshida, N., et al., *Chemical Abstracts* 105(20):181666b, 1986 of EP 186045, Jul. 2, 1986, 1,4–Dipyrimidinylbenzene Derivative and Liquid Crystal Composition Containing It.

Mikhaleva, M.A., et al., "Synthesis of 2,5'–substituted 2', 5–*bipyrimidine* Derivatives", *Chemical Abstracts* 114(7):62052z.

Kanbara, T., et al., "Preparation and Properties of Highly Electron–Accepting Poly(pyrimidine–2,5–diyl)", *Chemical Abstracts* 116(22):215028q.

(List continued on next page.)

Primary Examiner—Marie Yamnitzky
Attorney, Agent, or Firm—Frommmer Lawrence & Haug LLP

[57] ABSTRACT

The use of conjugated compounds which contain two or more pyrimidine rings as part of the conjugated system as electroluminescence materials. The conjugated compounds containing pyrimidine rings have a high thermal stability and a high photostability. They are partially soluble in acids, which also makes possible processing from solution, as well as by vapor deposition.

7 Claims, No Drawings

OTHER PUBLICATIONS

Asatryan, R.S., et al., "Heteroatom Effect on the Electrical Activity of Conjugated Polymers", *Chemical Abstracts* *109*(12):93976(e).

Tanaka, K., et al., "Design of Polymers with Metallic Properties: Substituted Polyperylene and Poly(p–phenylene)", *Chemical Abstracts* *107*(16):135025k.

Stankevich, I.V., "Existence of Isolated Energy Levels in .pi.–Electron Spectra of Macromolecules", *Chemical Abstracts* *82*(20):131179f.

USE OF CONJUGATED COMPOUNDS CONTAINING PYRIMIDINE GROUPS AS ELECTROLUMINESCENCE MATERIALS

DESCRIPTION

There is a great industrial need for large-area solid-state light sources for a series of applications, predominantly in the field of display elements, VDU technology and lighting engineering. The demands placed on these light sources can at present be completely satisfactorily met by none of the existing technologies.

As an alternative to conventional lighting and display elements, such as incandescent lamps, gas-discharge lamps and non-self-illuminating liquid crystal display elements, knowledge has existed for some time of electroluminescence (EL) materials and devices such as light-emitting diodes (LED).

Electroluminescence materials are substances which are capable of emitting light when an electric field is applied. The physical model for describing this effect is based on the radiative recombination of electrons and electron gaps ("holes"). In the case of light-emitting diodes, the charge carriers are injected into the electroluminescence material via the cathode or the anode. Electroluminescence devices comprise a luminescence material as light-omitting layer.

Electroluminescence materials and devices are described in general, for example, in Ullmann's Encyclopedia of Industrial Chemistry, Vol A9, 5th Ed. VCH Verlag 1987 and the literature cited therein.

Apart from inorganic materials such as ZnS/Mn or GaAs, organic compounds have also become known as EL materials. A description of EL devices comprising low molecular weight organic EL materials can be found, for example, in U.S. Pat. No. 4,539,507.

Disadvantages of these low molecular weight organic materials are, for example, the unsatisfactory film-forming properties and a pronounced tendency to crystallize.

Recently, polymers have also been described as EL materials (see, for example, WO-A 90/13148). However, the light yield (quantum efficiency) of these materials is considerably less than in the case of the low molecular weight compounds.

It was desirable to find EL materials which have good light yields and at the same time can be processed into thin homogeneous films with a low tendency to crystallize.

It has now surprisingly been found that conjugated compounds containing at least two pyrimidine rings are outstandingly suitable as electroluminescence materials.

The invention accordingly provides for the use of conjugated compounds containing two or more pyrimidine rings as part of the conjugated system as electroluminescence materials.

The conjugated compounds containing pyrimidine rings have high thermal stability and a high photostability. They are partially soluble in acids which makes possible processing from solution as well as vapor deposition.

Electroluminescence devices comprising the pyrimidine compounds of the invention have, among other things, a high color purity. The compounds used according to the invention allow, in particular, blue electroluminescence to also be achieved.

Preferred conjugated compounds containing two or more pyrimidine rings as part of the conjugated system are those of the formula (I),

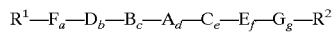

where the symbols and indices have the following meanings:

A
  is

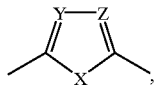

biphenyl-4,4'-diyl, anthracene-9,10-diyl, pyrimidine-2,5-diyl, 1,4-phenylene;

X
  is —O—, —CH=CH—, —CH=N—, —N=CH—;

Y, Z
  are identical or different and are —CR$^3$=, —N=;

B, C
  are identical or different and are pyrimidine-2,5-diyl, 1,4-phenylene, where one or two hydrogen atoms can be replaced by radicals R$^3$, pyridine-2,5-diyl, pyridinium-1,4-diyl, pyridinium-2,5-diyl, wherein the nitrogen atoms carries H, an alkyl group having from 1 to 20 carbon atoms or an unsubstituted or substituted phenyl group, —CR$^4$=CR$^5$—, —C≡C—;

D, E
  are identical or different and are A, B, C, —B—A—C—;

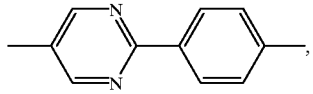

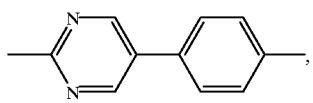

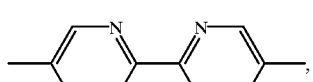

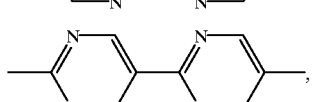

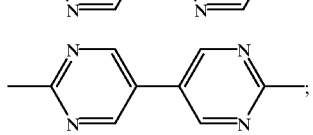

F, G
  are identical or different and are D, E, pyridine-2,5-diyl, pyridinium-1,4-diyl, pyridinium-2,5-diyl, wherein the nitrogen atom carries H, an alkyl group having from 1 to 20 carbon atoms or an unsubstituted or substituted phenyl group, 4-pyridyl;

R$^1$,R$^2$,R$^3$,R$^4$,R$^5$ are identical or different and are each H,
  an unbranched or branched alkyl group having from 1 to 12 carbon atoms, where one or more —CH$_2$— groups can be replaced by —O—, or are —CN, —NR$_2^6$;

R$^6$
  is H, an alkyl group having from 1 to 6 carbon atoms, phenyl;

a, c, d, e, g are identical or different and are 0 or 1;

b, f
are identical or different and are 0, 1 or 2; where the sum a+b+c+d+e+f+g must be at least 3 and the group —$F_a$—$D_b$—$B_c$—$A_d$—$C_e$—$E_f$—$G_g$— must contain at least 2 pyrimidine-2,5-diyl groups.

Preference is given to compounds of the formula (I) in which the symbols and indices have the following meanings:

A
is pyrimidine-2,5-diyl, 1,4-phenylene;

B, C
are identical or different and are pyrimidine-2,5-diyl, 1,4-phenylene, where one or two hydrogen atoms can be replaced by radicals $R^3$, —CH=CH—;

D, E
are identical or different and are A, B, C, —B—A—C—,

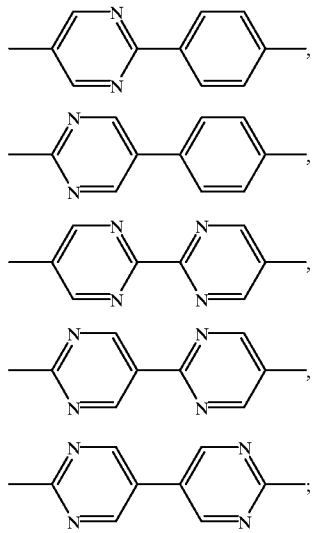

F, G
are identical or different and are D, E;

$R^1, R^2, R^3$ are identical or different and are each H, an unbranched or branched alkyl group having from 1 to 12 carbon atoms, where one —CH$_2$— group can be replaced by —O—, or are —CN, —NR$_2^6$;

$R^6$
is H, an alkyl group having from 1 to 6 carbon atoms, phenyl;

a, c, d, e, g are identical or different and are 0 or 1;

b, f
are identical or different and are 0, 1 or 2; where the sum a+b+c+d+e+f+g must be at least 3 and the group —$F_a$—$D_b$—$B_c$—$A_d$—$C_e$—$E_f$—$G_g$— must contain at least 2 pyrimidine-2,5-diyl groups.

Further preferred is the use of compounds of the formula (I) in which the sum a+b+c+d+e+f+g is at least 4, preferably from 4 to 9, particularly preferably from 5 to 9, very particularly preferably from 5 to 9.

Particular preference is given to compounds of the formula (I) in which the symbols and indices have the following meanings:

A
is pyrimidine-2,5-diyl, 1,4-phenylene;

B, C
are identical or different and are pyrimidine-2,5-diyl, 1,4-phenylene, —CH=CH—;

D, E
are identical or different and are A, B, C, —B—A—C—;

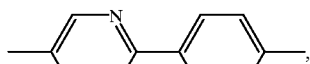

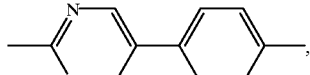

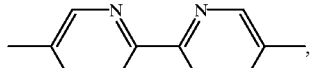

F, G
are identical or different and are D, E;

$R^1, R^2$
are each H, an unbranched or branched alkyl group having from 1 to 12 carbon atoms, —NR$_2^6$;

$R^6$
is H, an alkyl group having from 1 to 6 carbon atoms, phenyl;

a, c, d, e, g are identical or different and are 0 or 1;

b, f
are identical or different and are 0, 1 or 2; where the sum a+b+c+d+e+f+g must be at least 3 and the group —$F_a$—$D_b$—$B_c$—$A_d$—$C_e$—$E_f$—$G_g$— must contain at least 2 pyrimidine-2,5-diyl groups.

Very particular preference is given to compounds of the formula (I) in which the group —$F_a$—$D_b$—$B_c$—$A_d$—$C_e$—$E_f$—$G_g$— is selected from the group consisting of:

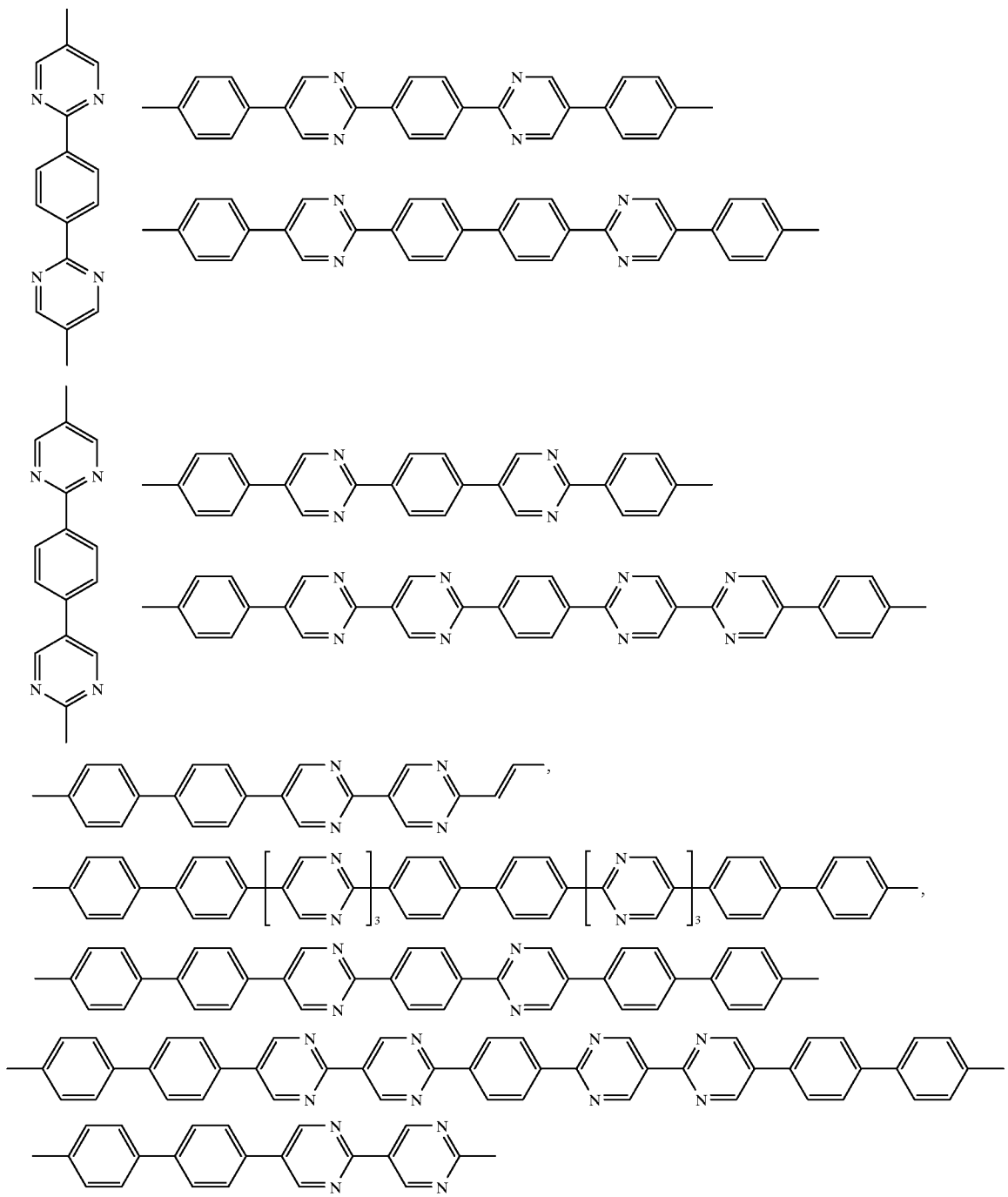

and $R^1$ and $R^2$ have the meanings given for formula (I).

Some of the compounds of the formula (I) are known and some are new.

The invention accordingly also provides pyrimidine compounds of the formula (I), where the symbols and indices have the meanings given there, with the condition that a) the sum a+b+c+d+e+f+g is at least 5, preferably from 5 to 9, particularly preferably from 5 to 9, and/or that b) the sum a+b+c+d+e+f+g is at least 3 and that the group $-F_a-D_b-B_c-A_d-C_e-E_f-G_g-$ contains at least 3 pyrimidine-2, 5-diyl groups.

Preferred and particularly preferred meanings for the symbols $R^1$ to $R^6$, A, B, C, D, E, F, G, X, Y, Z in the formula (I) of the compounds of the invention are those given above.

Pyrimidine compounds of the formula (I) which are preferred in particular are those in which the group $-F_a-D_b-B_c-A_d-C_e-E_f-G_g-$ is selected from the group:

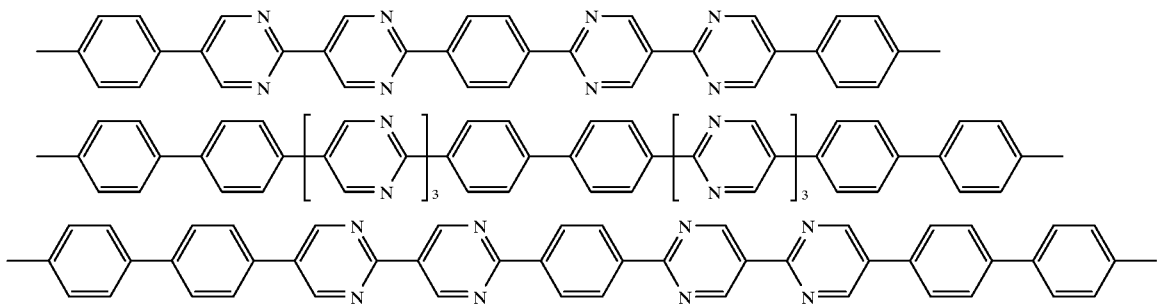

Compounds of the formula (I) of the invention or used according to the invention can be prepared by literature methods known per se, as are described in standard works on organic synthesis, e.g. Houben-Weyl, Methoden der Organischen Chemie, Georg-Thieme-Verlag, Stuttgart.

The preparation is here carried out under reaction conditions which are known and suitable for the specified reactions. In these reactions it is also possible to make use of variants which are known per se and are not mentioned further here.

The starting materials can, if desired, also be formed in situ, namely by not isolating them from the reaction mixture, but immediately reacting them further to give the compounds of the formula (I).

Reference may be made, for example, to DE-A 23 44 732, 24 50 088, 24 29 093, 25 02 94, 26 36 684, 27 01 591 and 27 52 975 for compounds containing 1,4-phenylene groups; DE-A 26 41 724 for compounds containing pyrimidine-2, 5-diyl groups; DE-A 40 26 223 and EP-A 0 391 203 for compounds containing pyridine-2,5-diyl groups.

The preparation of disubstituted pyridines and disubstituted pyrimidines is also given, for example, in the appropriate volumes of the series "The Chemistry of Heterocyclic Compounds" by A. Weissberger and E. C. Taylor (editors).

As regards the linking of the ring systems to one another, reference may be made, for example, to: N. Miyaura, T. Yanagai and A. Suzuki in Synthetic Communications 11 (1981) 513–519, DE-C-39 30 663, M. J. Sharp, W. Cheng, V. Snieckus in Tetrahedron Letters 28 (1987) 5093; G. W. Gray in J. Chem. Soc. Perkin Trans II 1989, 2041 and Mol. Cryst. Liq. Cryst. 172 (1989) 165; 204 (1991) 43 and 91; EP-A 0 449 015; WO-A 89/12039; WO-A 89/03821; EP-A 0 354 434 for the direct linking of aromatics and heteroaromatics and Koji Seto et al. in Liquid Crystals 8 (1990) 861 for compounds having —C≡C—bridges.

Compounds of the formula (I) can also be prepared, for example, by reaction of substituted aryl vinamidinium salts with amidines.

Using this pyrimidine synthesis principle as a basis, defined p-oligopyrimidines can be built up by repeated condensation of vinamidinium salts with amidines and subsequent renewed vinamidation (Scheme 1).

Scheme 1

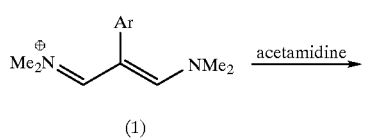

-continued

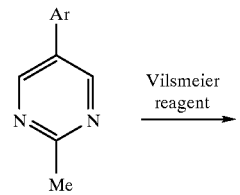

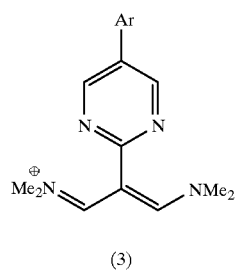

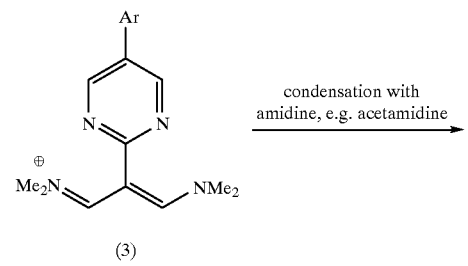

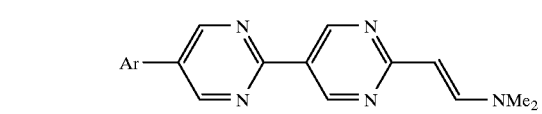

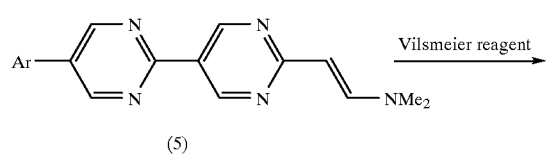

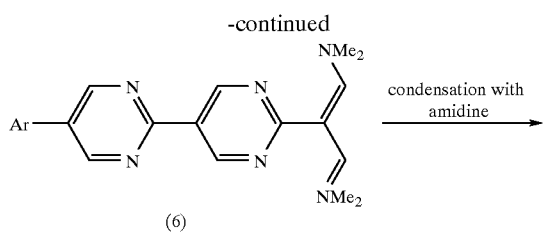

(6)

The heteroaryl vinamidinium salts (3) are prepared, for example, by reaction of methyl-substituted heteroaromatics (2) under the conditions of the Vilsmeier-Haack reaction (see, for example, de Meheas, Bull. Soc. Chim. Fr. (1962) 1989–1999), for example using dimethylformamide (DMF) and oxalyl chloride.

Methyl-substituted heteroaromatics (2) can be prepared by known methods from aryl-substituted vinamidinium salts (1) by condensation with suitable nitrogen compounds such as acetamidine. The vinamidinium salts (3) can be converted into the methyl-substituted compounds (4) by a similar method.

In the further build up of compounds of the formula (I) it is advantageous, for reasons of yield and purity of the products obtained, first to convert the methyl-substituted heteroaromatic (4) into the enamine (5) by reaction with, for example, the Bredereck's reagent (t-butyloxybis (dimethylamino)methane) and to subsequently prepare the vinamidinium salt (6) from the enamine under Vilsmeier-Haack conditions.

The vinamidinium salt (6) can be condensed to give higher oligomers of the formula (I) using methods known in the literature.

In the above described reactions, complex anions such as $PF_6^\ominus$, $BF_4^\ominus$ or $ClO_4^\ominus$ generally serve as counterions. Preference is given to using $ClO_4^\ominus$.

If vinamidinium salts (7) are reacted with arylenebis (pertrimethylsilyl)carbamidine (6) in a molar ratio of 2:1, based on the vinamidinium salt (7), with addition of a desilylation agent such as KF, there are obtained symmetrical pyrimidine compounds as a result of two-fold pyrimidine formation (Scheme 2).

Scheme 2

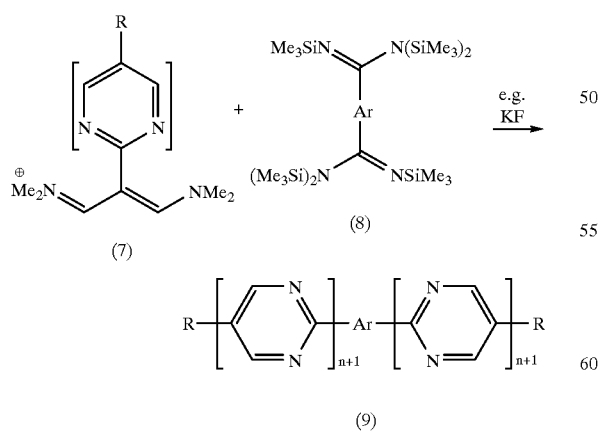

In a change of the synthesis strategy, arylenebisvinamidinium salts (10) can also be reacted with amidines. This enables the preparation of symmetrical pyrimidine compounds (11) having reversed pyrimidine polarity compared with the above example, with it being possible to further react (11) in a manner similar to the above Reaction Scheme 1 via the bisenamine (12) and the bisvinamidinium salt (13) to give defined higher oligomers of the formula (I) (Scheme 3).

Scheme 3

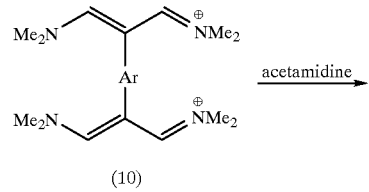

(10)

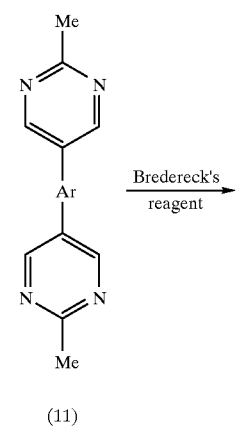

(11)

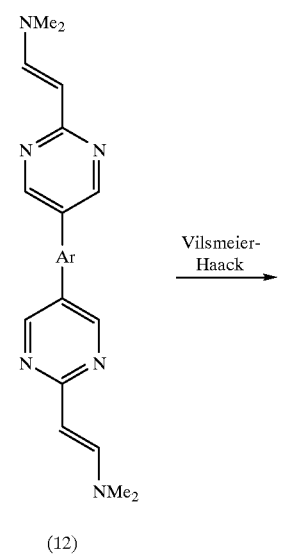

(12)

-continued

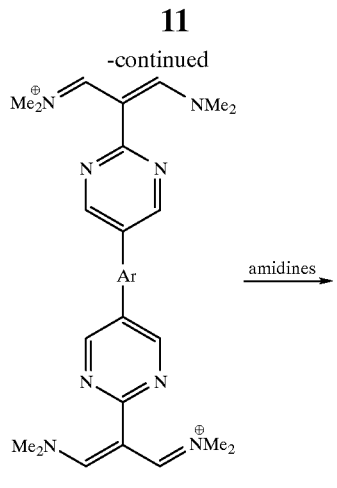

(13)

Compounds of the formula (I)

Compounds of the Formula (I)

The aryl groups (Ar in Schemes 1–3) can here be prepared by methods known per se in the literature, such as are described in standard works on organic synthesis, e.g. Houben-Weyl, Methoden der Organischen Chemie, Georg-Thieme-Verlag, Stuttgart and in the appropriate volumes of the series "The Chemistry of Heterocyclic Compounds" by A. Weissberger and E. C. Taylor (editors).

The invention therefore also provides a process for preparing 2,5'-bipyrimidine derivatives, which comprises converting a 2-methylpyrimidine derivative into the corresponding enamine using an enamination reagent, subsequently reacting the enamine with a Vilsmeier-Haack reagent to give the vinamidinium salt, if desired precipitating the latter with a complex anion and reacting the vinamidinium salt thus obtained with an amidine.

The process of the invention gives well-defined products in good yields and high purity. It is outstandingly suitable for the build up to 2,5'; 2',2"-terpyrimidine compounds and quite generally higher 2,5-linked oligopyrimidines.

The enamination reagents used according to the invention are known from the relevant literature, preference being given to t-butyloxybis(dimethylamino)methane (Bredereck's reagent), DMF/dimethyl sulfate or dimethylformamide acetals, particularly preferably the Bredereck's reagent.

The enamination reagent preferably also serves as solvent; however it is also possible to use mixtures of the enamination reagent and, for example, pyridine, DMSO, DMF, N-methylpyrrolidone, preferably pyridine.

The enamination reagent can be used in an equimolar amount or in excess; if it is used as solvent, a 1- to 100-fold, in particular a 1- to 5-fold, excess is preferred.

The enamination step generally proceeds at a temperature of from 100° to 200° C., preferably from 140 to 160° C.

The enamine can be worked up by methods known in the literature, as are indicated, inter alia, in the examples.

For the conversion into the vinamidinium salt, all customary Vilsmeier reagents are fundamentally suitable, such as $POCl_3$, oxalyl chloride, $COCl_2$, $O(SO_2-CF_3)_2$. Preference is given to using oxalyl chloride.

The reaction is usually carried out in DMF or mixtures of DMF and other suitable solvents such as methylene chloride, chloroform, or else in a multiphase system comprising DMF and solvents not miscible therewith, such as nitrobenzene.

The reaction is generally carried out at a temperature of from −60 to +100° C., preferably from −50 to +70° C.

Enamine and Vilsmeier reagent are usually used in a ratio of 1:1–3, preferably 1:1–2.

The workup is carried out using customary methods, some of which are described in the examples.

Well-defined vinamidinium salts can be advantageously prepared by precipitation with a complex anion such as $BF_4^\ominus$, $PF_6^\ominus$, $ClO_4^\ominus$, tetracyanopropenide, preferably $ClO_4^\ominus$.

The precipitation is generally carried out from water, with the precipitant preferably being used in an excess of up to 10-fold.

The vinamidinium salt thus obtained is further reacted with amidines known per se.

In general, the molar ratio of vinamidinium salt to amidine is 0.2–5:1, preferably 0.5–1:1.

The vinamidinium salt and an amidine are reacted in a solvent in the presence of a base, with solvent and base being able to be identical.

Examples of suitable solvents are pyridine, alcohols such as methanol, ethanol, water or else mixtures such as pyridine/acetic acid.

Suitable bases are, for example, pyridine, carbonates such as $K_2CO_3$, or alkoxides such as methoxide.

The reaction is usually carried out at a temperature of from 60 to 180° C., preferably from 80 to 120° C.

The 2,5'-bipyrimidine derivatives prepared according to the invention are worked up by methods known per se and familiar to those skilled in the art, as are described, inter alia, in the examples.

The invention further provides a process for preparing bispyrimidine or oligopyrimidine compounds, which comprises reacting a vinamidinium salt with a (hetero)arylenebis (pertrimethylsilyl)carbamidine compound in the presence of a desilylation agent in an organic solvent at a temperature of from 0 to 250° C.

Preferred starting compounds of the process of the invention are vinamidinium salts of the formula (II),

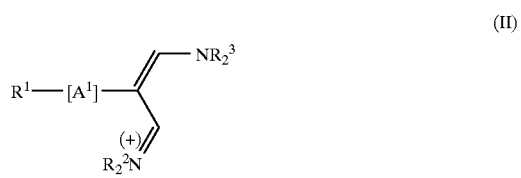

(II)

and (hetero)arylenebis(pertrialkylsilyl)carbamidine compounds of the formula (III),

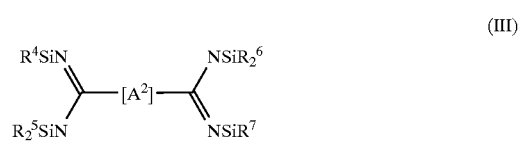

(III)

where the symbols with indices have the following meanings:

$A^1$, $A^2$
are identical or different and are 1,4-phenylene, pyrazine-2,5-diyl, pyridazine-3,6-diyl, pyridine-2,5-diyl, pyrimidine-2,5-diyl, 1,3,4-oxadiazole-2,5-diyl, 1,3-oxadiazole-2,4-diyl, 1,3-oxadiazole-2,5-diyl, 1,3,4-triazole-2,5-diyl, 1,3,4-thiadiazole-2,5-diyl, 1,3-thiazole-2,4-diyl, 1,3-thiazole-2,5-diyl, thiophene-2,4-diyl, thiophene-2,5-diyl, pyrrole-2,5-diyl, pyrrole-2,4-diyl, furan-2,5-diyl, furan-2,4-diyl, naphthalene-2,6-diyl;

$R^1, R^2, R^3, R^4, R^5$ are identical or different and are each H, an unbranched or branched alkyl group having from 1 to 12 carbon atoms, where one or more —CH$_2$— groups can be replaced by —O—, or are —CN, NR$_2^6$;

$R^6$ is H, an alkyl group having from 1 to 6 carbon atoms, phenyl.

All conceivable desilylation agents such as TiCl$_3$ or bases can be used. However, preferred desilylation agents are fluoride ions which are used in the form of an inorganic or organic fluoride, such as KF, NH$_4$F, Bu$_4$NF, preferably KF.

The desilylation agent is generally used in a stoichiometric amount or in an excess of up to 5-fold, preferably in a stoichiometric amount, based on the silyl groups present.

Suitable solvents for the process of the invention are, for example, dimethylformamide, pyridine, DMSO, N-methylpyrrolidone, alcohols or mixtures of these solvents.

Preference is given to using a mixture of pyridine/DMF, preferably in a ratio of 3/1.

The process of the invention is advantageously carried out at a temperature of from 0 to 200° C., preferably from 90 to 150° C.

The reaction time is generally from 3 to 15 hours.

The workup can be carried out by methods which are generally known and familiar to those skilled in the art, as are indicated, inter alia, in the examples.

According to the invention, the pyrimidine compounds of the formula (I) described are used as electroluminescence materials; i.e. they serve as active layer in an electroluminescence device. For the purposes of the present invention, an active layer is an electroluminescence material which is capable of radiating light on application of an electric field (light-emitting layer), or a material which improves the injection and/or the transport of the positive and/or negative charges (charge-injection layers and charge-transport layers).

The invention therefore also provides an electroluminescence device having one or more active layers which comprises one or more compounds of the formula (I). The active layer can, for example, be a light-emitting layer and/or a transport layer and/or a charge-injection layer.

The general structure of such electroluminescence devices is described, for example, in U.S. Pat. No. 4,539,507 and U.S. Pat. No. 5,151,629.

They customarily contain an electroluminescing layer between a cathode and an anode, with at least one of the electrodes being transparent. In addition, an electron-injection and/or electron-transport layer can be introduced between the electroluminescing layer and the cathode and/or a hole-injection and/or hole-transport layer can be introduced between the electroluminescing layer and the anode. Suitable cathodes are, for example, Ca, Mg, Al, In, Mg/Ag. Suitable anodes are, for example, Au or ITO (indium oxide/tin oxide on a transparent substrate, e.g. made of glass or a transparent polymer).

In operation, the cathode is placed at a negative potential with respect to the anode: in this way electrons from the cathode are injected into the electron-injection layer/electron-transport layer or directly into the light-emitting layer. At the same time, holes from the anode are injected into the hole-injection layer/hole-transport layer or directly into the light-emitting layer.

The injected charge carriers move toward one another through the active layers under the action of the applied potential. At the interface between charge-transport layer and light-emitting layer or within the light-emitting layer, this leads to electron/hole pairs which recombine with emission of light.

The color of the emitted light can be varied by means of the compound used as light-emitting layer.

Electroluminescence devices are used, for example, as self-illuminating display elements such as control lamps, alphanumeric displays, signs and in optoelectronic couplers.

The invention is illustrated by the examples, without being limited to them.

EXAMPLE 1

2-[2'-(5'-Phenyl)-pyrimidinyl]-3-dimethylamino-N,N-dimethyl-prop-2-eniminium perchlorate (14)

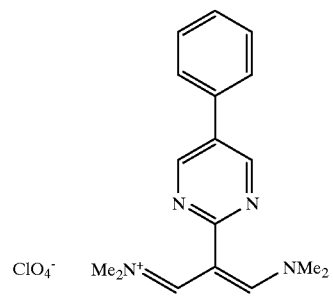

(14)

0.63 ml (7.34 mmol, 2.5 equivalents) of oxalyl chloride were added at −50° C. to 6.82 ml (88.13 mmol, 30 equivalents) of anhydrous DMF with vigorous stirring. After thawing for 20 minutes, 0.50 g (2.94 mmol) of 2-methyl-5-phenylpyrimidine were added to the reaction mixture (see R. M. Wagner, C. Jutz, Chem. Ber. 104 (1971) 2975) and the suspension was heated at 45° C. for 18 hours. After cooling, the reaction mixture was admixed with 10 ml of water, the clear solution obtained was subsequently slowly added dropwise at room temperature to 4.13 g (29.38 mmol, 10 equivalents) of sodium perchlorate monohydrate dissolved in 200 ml of water. The precipitate formed was filtered off with suction and washed with plenty of water. Yield: 0.94 g (84%) of beige microcrystalline powder. The purity of the crude product was found to be sufficient for most reactions; for analytical purposes, 0.30 g of the crude product was recrystallized from 50 ml of acetonitrile. Yield: 0.28 g (71%) of colorless crystals.

UV/VIS (DMSO): $\lambda_{max}$ (lg $\epsilon$)=313 nm (4.455). $^1$H-NMR ([D]TFA): δ=3.45 (s, 6H, 2 NCH$_3$), 3.76 (s, 6H, 2 NCH$_3$), 7.60–7.66 (m, 3H, Ph-3-H, Ph-4-H, Ph-5-H), 7.68–7.73 (m, 2H, Ph-2-H, Ph-6H), 8.40 (s, 2H, 1-H, 3-H), 9.29 (s, 2H, Pym).

C$_{17}$H$_{21}$ClN$_4$O$_4$ Calc. C 53.62 H 5.56 N 14.71 (380.8)
Found C 53.63 H 5.55 N 14.48

EXAMPLE 2

2,2'-(p-Phenylene)dipyrimidine (15)

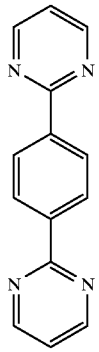
(15)

A suspension of 1.50 g (6.62 mmol) of 3-dimethylamino-N,N-dimethylprop-2-eniminium perchlorate (S. S. Malhotra, M. C. Whiting, J. Chem. Soc. (1960) 3812) and 1.97 g (3.31 mmol, 0.5 equivalent) of phenylene-1,4-bis(pertrimethylsilylcarbamidine) (R. T. Boere, R. T. Oakley, R. W. Reed, J. Organomet. Chem. 331 (1987) 161) in 35 ml of pyridine was, with addition of 1.15 g (19.85 mmol, 3 equivalents) of potassium fluoride, heated under reflux for 6 hours. The precipitate, part of which had already formed during heating, was filtered off with suction after cooling, washed with plenty of water and subsequently with methanol. The colorless crude product was recrystallized from 120 ml of DMSO. Yield: 0.64 g (81%) of colorless platelets, m.p.>330° C.

UV/VIS (DMSO): $\lambda_{max}$ (lg ϵ)=294 nm (4.308). Fluorescence (DMSO): $\lambda_{max}$ =367 nm $^1$H-NMR ([D]TFA): δ=8.20 (t, J=6 Hz, 2H Pym-5-H), 8.74 (s, 4H, Phn), 9.50 (d, J=6 Hz, 4H, Pym-4-H, Pym-6-H).

$C_{14}H_{10}N_4 \cdot \frac{1}{3}H_2O$ Calc. C 69.99 H 4.44 N 23.32 (240.3) Found C 69.99 H 4.37 N 23.09

EXAMPLE 3

5,5'-Bis(phenyl)-2,2'-(p-phenylene)dipyrimidine (16)

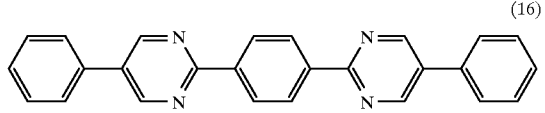
(16)

A suspension of 1.50 g (4.95 mmol) of 2-phenyl-3-dimethylamino-N,N-dimethylprop-2-eniminium perchlorate (S. N. Balasubrahmanyam, A. S. Radhakrishna, J. Chem. Soc., Perkin Trans. 2 (1977) 1388) and 1.47 g (2.48 mmol, 0.5 equivalent) of phenylene-1,4-bis(pertrimethylsilylcarbamidine) (R. T. Boere, R. T. Oakley, R. W. Reed. J. Organomet. Chem. 331 (1987) 161) in 50 ml of pyridine was, with addition of 0.86 g (14.86 mmol, 3 equivalents) of potassium fluoride, heated under reflux for 5 hours. The precipitate, part of which had already appeared during heating, was filtered off with suction after cooling, washed with plenty of water and subsequently with methanol. The colorless crude product was recrystallized from 150 ml of DMSO. Yield: 0.88 g (92%) of colorless crystalline platelets, m.p.>330° C.

UV/VIS (DMSO): $\lambda_{max}$ (lg ϵ)=332 nm (4.342). Fluorescence (DMSO): $\lambda_{max}$ =398 nm $^1$H-NMR ([D]TFA): δ=7.69–7.75 (m, 6H, Ph-3-H, Ph-4-H, Ph-5-H), 7.82–7.87 (m, 4H, Ph-2-H, Ph-6-H), 8.79 (s, 4H, Phn), 9.67 (s, 4H, Pym).

$C_{26}H_{18}N_4$ Calc. C 80.81 H 4.69 N 14.50 (386.5) Found C 81.11 H 4.70 N 14.22

EXAMPLE 4

5,5'-Bis(phenyl)-2,2'-(p-biphenylene)dipyrimidine (17)

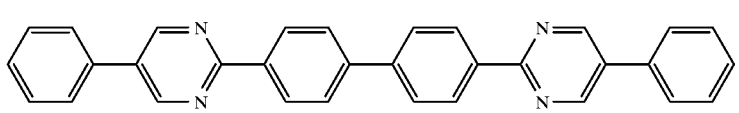
(17)

A suspension of 1.50 g (4.95 mmol) of 2-phenyl-3-dimethylamino-N,N-dimethylprop-2-eniminium perchlorate (see S. N. Balasubrahmanyam, A. S. Radhakrishna, J. Chem. Soc., Perkin Trans. 2 (1977) 1388) and 1.66 g (2.48 mmol, 0.5 equivalent) of 1,1'-biphenylene-4,4'-bis(pertrimethylsilylcarbamidine) (prepared by a similar method to phenylene-1,4-bis(pertrimethylsilylcarbamidine)) in 60 ml of pyridine was, with addition of 0.86 g (14.86 mmol, 3 equivalents) of potassium fluoride, heated under reflux for 5 hours. The precipitate, part of which had already appeared during heating, was filtered off with suction after cooling, washed with plenty of water and subsequently with acetone. The colorless crude product was recrystallized from 200 ml of DMSO. Yield: 1.02 g (89%) of colorless platelets, m.p.>330° C.

UV/VIS (DMSO): $\lambda_{max}$ (lg ϵ)=336 nm (4.306). Fluorescence (DMSO): $\lambda_{max}$ =382.397 nm $^1$H-NMR ([D]TFA): δ=7.66–7.73 (m, 6H, Ph-3-H, Ph-4-H, Ph-5-H), 7.78–7.84 (m, 4H, Ph-2-H, Ph-6-H), AA'BB' signal centered at 8.14 ($^3$J=8 Hz, 4H, Biphn-2-H, Biphn-6-H) and 8.59 ($^3$J=8 Hz, 4H, Biphn-3-H, Biphn-5-H), 9.59 (s, 4H, Pym).

EXAMPLE 5

2,2'-Bis(phenyl)-5,5'-(p-phenylene)dipyrimidine (18)

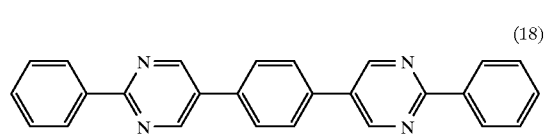
(18)

1.00 g (1.90 mmol) of phenylene-1,4-bis(3-dimethylamino-N,N-dimethylprop-2-eniminium perchlorate (Z. Arnold, Collect. Czech. Chem. Commun. 30 (1965) 2783) was heated under reflux for 5 hours with 0.74 g (4.74 mmol, 2.5 equivalents) of benzamidine hydrochloride hydrate in 40 ml of pyridine. After cooling, the precipitate formed was filtered off with suction and washed with plenty of water and subsequently with methanol. Recrystallization of the pale brown crude product from 70 ml of DMSO gave colorless platelets. Yield: 0.66 g (90%), m.p. 299° C.

UV/VIS (DMSO): $\lambda_{max}$ (lg $\epsilon$)=321 nm (4.680). Fluorescence (DMSO): $\lambda_{max}$ =437 nm $^1$H-NMR ([D]TFA): $\delta$=AA'BB'C signal centered at 7.78 ($^3$J=8 Hz, 4H, Ph-3-H, Ph-5-H), at 7.91 ($^3$J=8 Hz, 2H, Ph-4-H) and at 8.44 ($^3$J=8 Hz, 4H, Ph-2-H, Ph-6-H), 8.14 (s, 4H, Phn), 9.67 (s, 4H, Pym).

EXAMPLE 6

5,5'-(p-Phenylene)dipyrimidine (19)

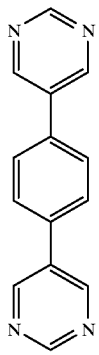

(19)

2.00 g (3.79 mmol) of phenylene-1,4-bis(3-dimethylamino-N,N-dimethylprop-2-eniminium perchlorate) (Z. Arnold, Collect. Czech. Chem. Commun. 30 (1965) 2783) were heated under reflux for 12 hours with 0.92 g (11.38 mmol, 3 equivalents) of formamidine hydrochloride in 30 ml of pyridine. After cooling, the precipitate formed was filtered off with suction, washed with water and methanol and recrystallized from 50 ml of DMSO. Yield: 0.68 g (77%) of colorless platelets, m.p. 258° C.

UV/VIS (DMSO): $\lambda_{max}$ (lg $\epsilon$)=279 nm (4.374). Fluorescence (DMSO): $\lambda_{max}$ =428 nm $^1$H-NMR ([D]TFA): $\delta$=8.15 (s, 4H, Phn), 9.81 (s, 4H, Pym-4-H, Pym-6-H), 9.84 (s, 2H, Pym-2-H).

$C_{14}H_{10}N_4$ Calc. C 71.78 H 4.30 N 23.92 (234.3) Found C 71.72 H 4.33 N 23.79

EXAMPLE 7

5,5''-Bis(phenyl)-2',2'''-(p-phenylene)di(2,5'-bipyrimidine) (20)

The suspension of 0.80 g (2.10 mmol) of vinamidinium salt (14) and 0.63 g (1.05 mmol, 0.5 equivalent) of phenylene-1,4-bis(pertrimethylsilylcarbamidine) (R. T. Boere, R. T. Oakley, R. W. Reed, J. Organomet. Chem 331 (1987) 161.) was heated under reflux for 10 hours in a mixture of 30 ml of pyridine and 10 ml of DMF with addition of 0.37 g (6.30 mmol, 3 equivalents) of potassium fluoride. The precipitate, which had already appeared during heating, was filtered off with suction after cooling, washed with plenty of water and subsequently with acetone. Yield: 0.54 g (95%) of colorless powder. Recrystallization of 0.03 g of crude product from 250 ml of DMSO gave a virtually quantitative yield. Colorless powder, m.p.>330° C.

UV/VIS (DMSO): $\lambda_{max}$ (lg $\epsilon$)=346 nm, 396 nm (qual.). Fluorescence (DMSO):$\lambda_{max}$ =489 nm $^1$H-NMR ([D]TFA): $\delta$=7.67–7.72 (m, 6H, Ph-3-H, Ph-4-H, Ph-5-H), 7.81–7.86 (m, 4H, Ph-2-H, Ph-6-H), 8.85 (s, 4H, Phn), 9.62 (s, 4H, Pym), 10.36 (s, 4H, Pym').

$C_{34}H_{22}N_8$ Calc. C 75.26 H 4.09 N 20.65 (542.6) Found C 75.19 H 4.07 N 20.55

EXAMPLE 8

2-(p-Biphenyl)-3-dimethylamino-N,N-dimethylprop-2-eniminium perchlorate (21)

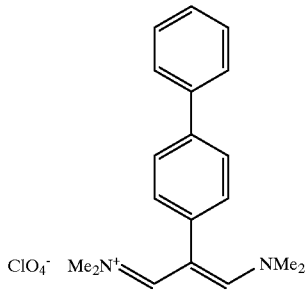

(21)

16.47 ml (176.68 mmol, 2.5 equivalents) of phosphorus oxychloride were added dropwise at 0° C. to 54.73 ml (706.71 mmol, 10 equivalents) of anhydrous DMF and the reaction mixture was stirred for 30 minutes at 0° C. 15.00 g (70.67 mmol) of 4-biphenylacetic acid were subsequently added and the mixture was heated at 110° C. for 18 hours. After cooling, the reaction mixture was admixed with 70 ml of water, a solution of 29.78 g (212.01 mmol, 3 equivalents) of sodium perchlorate monohydrate in 300 ml of water was added at room temperature and the precipitate thus formed was filtered off with suction and washed with plenty of water. Yield: 21.13 g (78%) of beige powder.

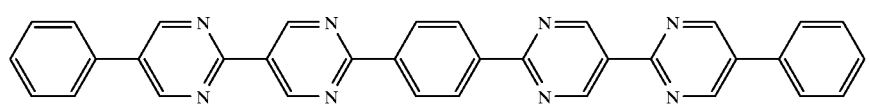

(20)

$^1$H-NMR ([D]TFA): $\delta$=2.65 (s, 6H, 2 NCH$_3$), 3.34 (s, 6H, 2 NCH$_3$), 7.34–7.49 (m, 7H, 1-H, 3-H and Ph), AA'BB' signal centered at 7.67 ($^3$J=8 Hz, 2H, PhCCH) and 7.77 ($^3$J=8 Hz, 2H, PhCCHCH).

$C_{19}H_{23}ClN_2O_4 \cdot \frac{1}{4}H_2O$ Calc. C 59.53 H 6.18 N 7.31 (383.4) Found C 59.41 H 5.99 N 7.09

EXAMPLE 9

5-(p-Biphenyl)-2-methylpyrimidine (22)

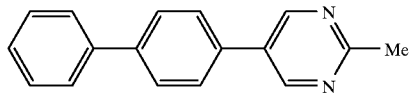

(22)

2.00 g (5.22 mmol) of vinamidinium salt (21) were heated under reflux for 15 hours with 0.74 g (7.83 mmol, 1.5 equivalents) of acetamidine hydrochloride in 20 ml of pyridine. After cooling, the mixture was admixed with 10 ml of methanol and the precipitate thus formed was filtered off with suction and washed with water. It was recrystallized from 80 ml of methanol.

Yield: 1.02 g (79%) of colorless powder, m.p. 206° C.

$^1$H-NMR ([D]TFA): δ=3.18 (s, 3H, CH$_3$), AA'BB'C signal centered at 7.41 ($^3$J=8 Hz, 1H, Ph-4-H), 7.48 ($^3$J=8 Hz, 2H, Ph-3-H, Ph-5-H) and 7.66 ($^3$J=8 Hz, 2H, Ph-2-H, Ph-6-H), AA'BB' signal centered at 7.79 ($^3$J=8 Hz, 2H, PhCCH) and 7.88 ($^3$J=8 Hz, 2H, PhCCHCH), 9.51 (s, 2H, Pym).

C$_{17}$H$_{14}$N$_2$ Calc. C 82.90 H 5.73 N 11.37 (246.3) Found C 83.02 H 5.66 N 11.11

EXAMPLE 10

5,5'-Bis(p-biphenyl)-2,2'-(p-phenylene)dipyrimidine (23)

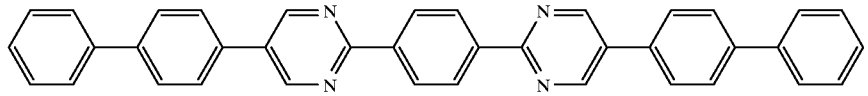

(23)

The suspension of 2.00 g (5.22 mmol) of vinamidinium salt (21) and 1.55 g (2.61 mmol, 0.5 equivalent) of phenylene-1,4-bis(pertrimethylsilylcarbamidine) (R. T. Boere, R. T. Oakley, R. W. Reed, J. Organomet. Chem. 331 (1987) 161) was heated under reflux for 12 hours in a mixture of 45 ml of pyridine and 15 ml of DMF with addition of 0.91 g (15.65 mmol, 3 equivalents) of potassium fluoride. The precipitate, which already appeared during heating, was filtered off with suction after cooling, washed with plenty of water and subsequently with acetone. Yield: 1.34 g (94%) of pale yellow powder. Recrystallization of 0.03 g of crude product from 200 ml of DMSO gave a virtually quantitative yield. Colorless powder, m.p.>330° C.

UV/VIS (DMSO): λ$_{max}$ (lg ε)=347 nm, (qual.). Fluorescence (DMSO): λ$_{max}$ =424 nm C$_{38}$H$_{26}$N$_4$·½H$_2$O Calc. C 83.34 H 4.97 N 10.23 (547.7) Found C 83.47 H 4.94 N 10.19

EXAMPLE 11

2-[2'-(5'-{p-Biphenyl})pyrimidinyl]-3-dimethylamino-N,N-dimethylprop-2-eniminium perchlorate (24)

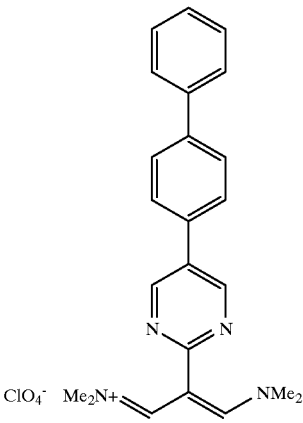

(24)

0.63 ml (6.09 mmol, 3 equivalents) of oxalyl chloride was added dropwise at −50° C. to 11.00 ml (142.10 mmol, 70 equivalents) of anhydrous DMF with vigorous stirring. After thawing for 20 minutes, 0.50 g (2.03 mmol) of methylpyrimidine (22) was added to the reaction mixture; the suspension was heated at 50° C. for 28 hours. After cooling, the reaction mixture was admixed with 15 ml of water, the clear solution obtained was subsequently slowly added dropwise at room temperature to 2.85 g (20.30 mmol, 10 equivalents) of sodium perchlorate monohydrate dissolved in 200 ml of water. The precipitate thus formed was filtered off with suction and washed with plenty of water and methanol. Yield: 0.80 g (86%) of beige microcrystalline powder.

UV/VIS (DMSO): λ$_{max}$ (lg ε)=321 nm (4.482), sh 380 nm (3.894)

$^1$H-NMR ([D]TFA): δ=3.45 (s, 6H, 2 NCH$_3$), 3.76 (s, 6H, 2 NCH$_3$), AA'BB'C signal centered at 7.41 ($^3$J=8 HZ, 1H, Ph-4-H), 7.47 ($^3$J=8 Hz, 2H, Ph-3-H, Ph-5-H) and 7.65 ($^3$J=8 Hz, 2H, Ph-2-H, Ph-6-H), AA'BB' signal centered at 7.77 ($^3$J=8 Hz, 2H, PhCCH) and 7.85 ($^3$J=8 Hz, 2H, PhCCHCH), 8.39 (s, 2H, 1-H, 3-H), 9.31 (s, 2H, Pym).

C$_{23}$H$_{25}$ClN$_4$O$_4$ Calc. C 60.46 H 5.51 N 12.26 (456.9) Found C 61.13 H 5.53 N 12.23

EXAMPLE 12

5-(p-Biphenyl)-2'-methyl-2,5'-bipyrimidine (25)

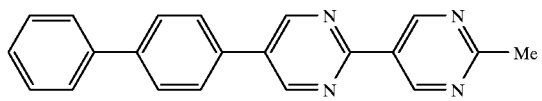

(25)

1.34 g (2.93 mmol) of vinamidinium salt (24) were heated under reflux for 12 hours with 0.42 g (4.40 mmol, 1.5 equivalents) of acetamidine hydrochloride in 25 ml of pyridine. After cooling, the mixture was admixed with 10 ml of methanol. The precipitate formed was filtered off with suction, washed with plenty of water and methanol and recrystallized from 50 ml of DMSO. Yield: 0.79 g (83%) of pale yellow powder, m.p. 250° C.

UV/VIS (DMSO): $\lambda_{max}$ (lg $\epsilon$)=311 nm (4.437), 424 (3.239). $^1$H-NMR ([D]TFA): $\delta$=3.26 (s, 3H, CH$_3$), AA'BB'C signal centered at 7.42 ($^3$J=8 Hz, 1H, Ph-4-H), 7.49 ($^3$J=8 Hz, 2H, Ph-3-H, Ph-5-H) and 7.70 ($^3$J=8 Hz, 2H, Ph-2-H, Ph-6-H), AA'BB' signal centered at 7.88 ($^3$J=8 Hz, 2H, PhCCH) and 7.92 ($^3$J=8 Hz, 2H, PhCCHCH), 9.57 (s, 2H, Pym), 10.20 ppm (s, 2H, Pym').

C$_{21}$H$_{16}$N$_4$ Calc. C 77.76 H 4.97 N 17.27 (324.4) Found C 77.64 H 4.89 N 17.12

EXAMPLE 13

5,5''-Bis(p-biphenyl)-2',2'''-(p-phenylene)di(2,5'-bipyrimidine) (26)

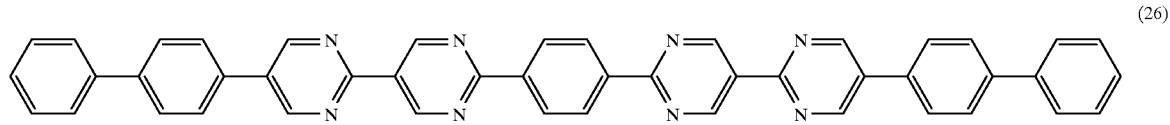

(26)

The suspension of 0.70 g (1.53 mmol) of vinamidinium salt (24) and 0.46 g (0.77 mmol, 0.5 equivalent) of phenylene-1,4-bis(pertrimethylsilylcarbamidine) (R. T. Boere, R. T. Oakley, R. W. Reed, J. Organomet. Chem 331 (1987) 161.) was, with addition of 0.27 g (4.60 mmol, 3 equivalents) of potassium fluoride, heated under reflux for 15 hours in a solvent mixture comprising 25 ml of pyridine and 15 ml of DMF. The very fine precipitate, which had already appeared during heating, was filtered off with suction after cooling, washed with DMF, plenty of water and acetone. Yield: 0.50 g (94%) of pale yellow powder, m.p.>330° C.

MS (70 eV), m/e (%): 694 (100) [M$^+$].

EXAMPLE 14

5-(p-Biphenyl)-2'-(2''-dimethylaminoethenyl)-2,5'-bipyrimidine (27)

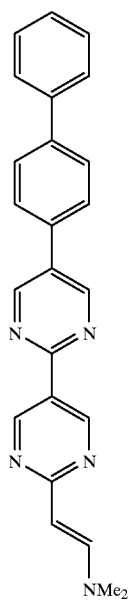

(27)

0.34 g (1.05 mmol) of methylbipyrimidine (25) was heated at 150° C. for 24 hours with 2.14 ml (10.48 mmol, 10 equivalents) of tert-butyloxybisdimethylaminomethane (Bredereck's reagent) with gentle stirring. After cooling, the mixture was admixed with 10 ml of isopropanol. The precipitate formed was filtered off with suction and washed with isopropanol and a little dichloromethane.

Yield: 0.33 g (82%) of yellow crystalline powder, melting point 284° C.

UV/VIS (DMSO): $\lambda_{max}$ (lg $\epsilon$)=297 nm (4.263), 407 (4.780). $^1$H-NMR ([D]TFA): $\delta$=3.33 (s, 3H, CH$_3$), 3.56 (s, 3H, CH$_3$), AA'BB'C signal centered at 7.44 ($^3$J=8 Hz, 1H, Ph-4-H), 7.51 ($^3$J=8 Hz, 2H, Ph-3-H, Ph-5-H) and 7.70 ($^3$J=8 Hz, 2H, Ph-2-H, Ph-6-H), AA'BB' signal centered at 7.86 ($^3$J=8 Hz, 2H, PhCCH) and 7.94 ($^3$J=8 Hz, 2H, PhCCHCH), 8.73 (s, 1H, (H$_3$C)$_2$—NCH), AB signal centered at 9.30 ($^4$J=3 Hz, 1H, Pym') and 9.53 ($^4$J=3 Hz, 1H, Pym')-protonated pyrimidine (cf. vinamidinium salt), 9.52 (s, 2H, Pym).

C$_{24}$H$_{21}$N$_5$ Calc. C 75.97 H 5.58 N 18.46 (379.5) Found C 75.86 H 5.59 N 18.52

EXAMPLE 15

2-[2''-(5'-p-Biphenyl)-2',5''-bipyrimidinyl]-3-dimethylamino-N,N-dimethylprop-2-eniminium perchlorate (28)

(28)

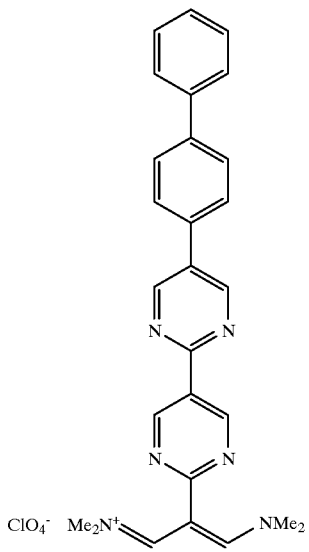

0.11 ml (1.26 mmol, 1.5 equivalents) of oxalyl chloride was added dropwise at −50° C. to 4.54 ml (59.03 mmol, 70 equivalents) of anhydrous DMF with vigorous stirring. 0.32 g (0.84 mmol) of enamine (27) was subsequently added to this reaction mixture; the suspension obtained was stirred for 6 hours at −50° C. After slow thawing, the mixture was admixed with 10 ml of water and the clear solution obtained was slowly added dropwise at room temperature to 1.18 g (8.43 mmol, 10 equivalents) of sodium perchlorate monohydrate dissolved in 100 ml of water. The precipitate thus formed was filtered off with suction and washed with plenty of water and methanol. Yield: 0.36 g (80%) of beige microcrystalline powder.

UV/VIS (DMSO): $\lambda_{max}$ (lg $\epsilon$)=360 nm (4.505), sh 429 (3.907).

$^1$H-NMR ([D]TFA): δ=3.54 (s, 6H, 2 NCH$_3$), 3.85 (s, 6H, 2 NCH$_3$), AA'BB'C signal centered at 7.42 ($^3$J=8 Hz, 1H, Ph-4-H), 7.49 ($^3$J=8 Hz, 2H, Ph-3-H, Ph-5-H) and 7.70 ($^3$J=8 Hz, 2H, Ph-2-H, Ph-6-H), AA'BB' signal centered at 7.88 ($^3$J=8 Hz, 2H, PhCCH) and 7.93 ($^3$J=8 Hz, 2H, PhCCHCH), 8.65 (s, 2H, 1-H, 3-H), 9.61 (s, 2H, Pym'), 9.96 (s, 2H, Pym").

EXAMPLE 16

5,5'''-Bis(p-biphenyl)-2'',2''''''-(p-biphenylene)di-(2,5';-2', 5''-terpyrimidine) (29)

(29)

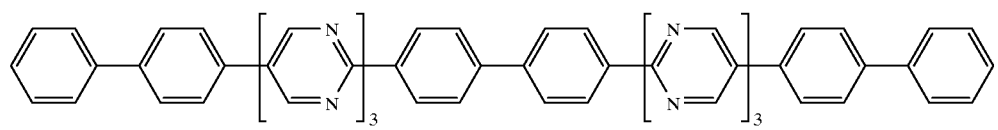

A suspension of 0.34 g (0.64 mmol) of vinamidinium salt (28) and 0.21 g (0.32 mmol, 0.5 equivalent) of 1,1'-biphenylene-4,4'-bis(pertrimethylsilylcarbamidine) was, with addition of 0.11 g (1.91 mmol, 3 equivalents) of potassium fluoride, heated under reflux for 15 hours in a solvent mixture of 20 ml of pyridine and 15 ml of DMF. The very fine precipitate, which had already appeared during heating, was filtered off with suction after cooling and washed with DMF, plenty of water and acetone. The product was subsequently boiled out with DMSO. Yield: 0.27 g (92%) of brownish yellow powder, m.p.>330° C.

UV/VIS (TFA): $\lambda_{max}$ (lg $\epsilon$)=386 nm (4.892). - MS (70 eV), m/e (%): 926 (55) [M$^+$]

We claim:

1. An electroluminescence material, which comprises a conjugated compound containing 2 or more pyrimidine rings as part of the conjugated system, wherein the conjugated compound has the formula (I), $$R^1-F_a-D_b-B_c-A_d-C_e-E_f-G_g-R^2 \qquad (I)$$

where the symbols and indices have the following meanings:

A is

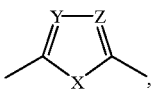

biphenyl-4,4'-diyl, anthracene-9,10-diyl, pyrimidine-2,5-diyl or 1,4-phenylene;

X is —O—, —CH=CH—, —CH=N— or —N=CH—;

Y and Z are identical or different and are —CR$^3$= or —N=;

B and C are identical or different and are: pyrimidine-2,5-diyl or 1,4-phenylene, where one or two hydrogen atoms can be replaced by radicals R$^3$; pyridine-2,5-diyl; pyridinium-1,4-diyl or pyridinium-2,5-diyl, wherein the nitrogen atom carries H, an alkyl group having from 1 to 20 carbon atoms or an unsubstituted or substituted phenyl group; —CR$^4$=CR$^5$—; or —C≡C—;

D and E are identical or different and are A, B, C, —B—A—C—,

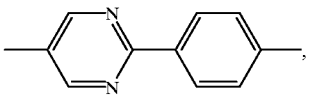

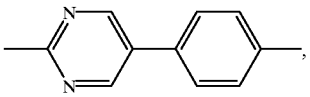

-continued

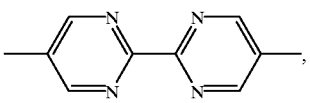

-continued

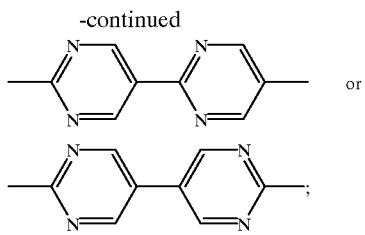

F and G
  are identical or different and are D, E; pyridine-2,5-diyl; pyridinium-1,4-diyl or pyridinium-2,5-diyl, wherein the nitrogen atom carries H, an alkyl group having from 1 to 20 carbon atoms or an unsubstituted or substituted phenyl group; or 4-pyridyl;
$R^1, R^2, R^3, R^4$ and $R^5$ are identical or different and are each H; an unbranched or branched alkyl group having from 1 to 12 carbon atoms; or $-NR^6{}_2$;
$R^6$
  is H, an alkyl group having from 1 to 6 carbon atoms or phenyl;
a, c, d, e and g are identical or different and are 0, or 1;
b and f are identical or different and are 0, 1 or 2; where the sum a+b+c+d+e+f+g must be at least 4 and the group $-F_a-D_b-B_c-A_d-C_e-E_f-G_g-$ must contain at least 2 pyrimidine-2,5-diyl groups.

2. The electroluminescence material as claimed in claim 1, wherein the symbols and indices in the formula (I) have the following meanings:
A
  is pyrimidine-2,5-diyl or 1,4-phenylene;
B and C
  are: identical or different and are pyrimidine-2,5-diyl or 1,4-phenylene, where one or two hydrogen atoms can be replaced by radicals $R^3$; or $-CH=CH-$;
D and E
  are identical or different and are A, B, C, $-B-A-C-$,

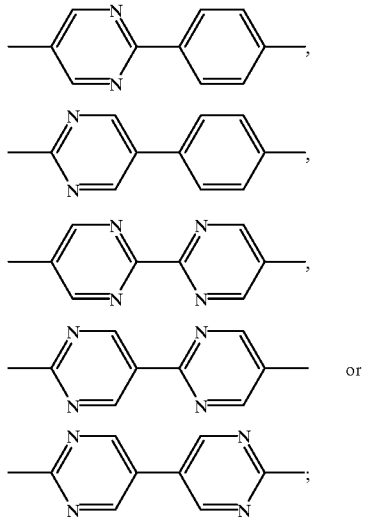

F and G
  are identical or different and are D or E,
$R^1$, $R^2$ and $R^3$ are identical or different and are each H; an unbranched or branched alkyl group having from 1 to 12 carbon atoms; $-NR^6{}_2$;
$R^6$
  is H, an alkyl group having from 1 to 6 carbon atoms or phenyl;
a, c, d, e and g are identical or different and are 0 or 1;
b and f
  are identical or different and are 0, 1 or 2; where the sum a+b+c+d+e+f+g must be at least 4 and the group $-F_a-D_b-B_c-A_d-C_e-E_f-G_g-$ must contain at least 2 pyrimidine-2,5-diyl groups.

3. The electroluminescence material as claimed in claim 1, wherein the symbols and indices in the formula (I) have the following meanings:
A
  is pyrimidine-2,5-diyl or 1,4-phenylene;
B and C
  are: identical or different and are pyrimidine-2,5-diyl; 1,4-phenylene or $-CH=CH-$;
D and E
  are identical or different and are A, B, C, $-B-A-C-$,

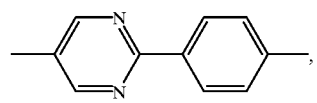

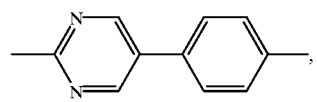

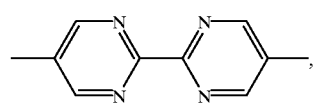

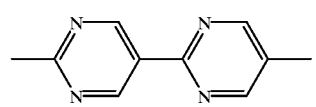

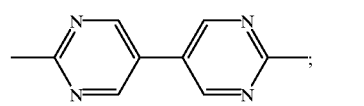

F and G
  are identical or different and are D or E,
$R^1$ and $R^2$
  are each H, an unbranched or branched alkyl group having from 1 to 12 carbon atoms, or $-NR^6{}_2$;
$R^6$
  is H, an alkyl group having from 1 to 6 carbon atoms, or phenyl;
a, c, d, e and g are identical or different and are 0 or 1;
b and f
  are identical or different and are 0, 1 or 2; where the sum a+b+c+d+e+f+g must be at least 4 and the group $-F_a-D_b-B_c-A_d-C_e-E_f-G_g-$ must contain at least 2 pyrimidine-2,5-diyl groups.

4. The electroluminescence material as claimed in claim 1, wherein the group in the $-F_a-D_b-B_c-A_d-C_e-E_f-G_g-$ in the formula (I) is selected from the group consisting of:

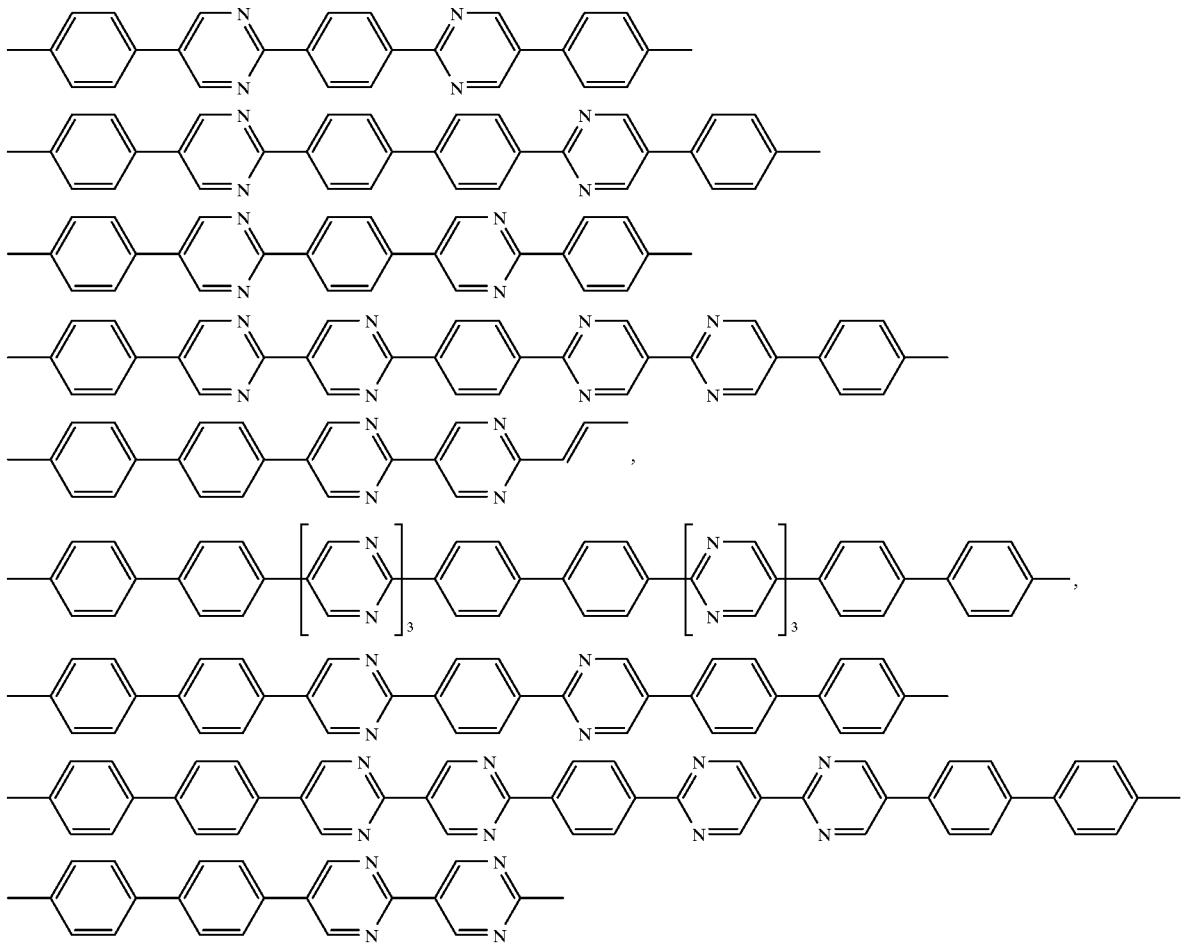

and $R^1$ and $R^2$ have the meanings given for the formula (I).

5. An electroluminescence device comprising as an active layer an electroluminescence material having a conjugated compound containing 2 or more pyrimidine rings as part of the conjugated system as claimed in claim 1.

6. A pyrimidine compound of the formula (I), $$R^1-F_a-D_b-B_c-A_d-C_e-E_f-G_g-R^2 \quad (I)$$

where the symbols and indices have the following meanings:

A is

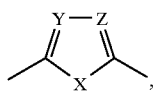

biphenyl-4,4'-diyl, anthracene-9,10-diyl, pyrimidine-2,5-diyl or 1,4-phenylene;

X
is —O—, —CH=CH—, —CH=N— or —N=CH—;

Y and Z
are identical or different and are —CR³= or —N=;

B and C
are: identical or different and are pyrimidine-2,5-diyl or 1,4-phenylene, where one or two hydrogen atoms can be replaced by radicals $R^3$; pyridine-2,5-diyl; pyridinium-1,4-diyl or pyridinium-2,5-diyl, wherein the nitrogen atom carries H, an alkyl group having from 1 to 20 carbon atoms or an unsubstituted or substituted phenyl group; —CR⁴=CR⁵—; or —C≡C—;

D and E
are identical or different and are A, B, C, —B—A—C—,

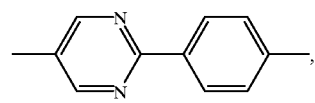

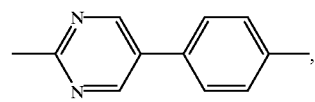

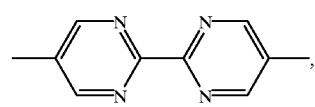

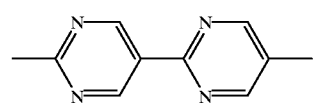 or

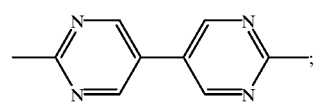

F and G are identical or different and are D; E; pyridine-2,5-diyl; pyridinium-1,4-diyl or pyridinium-2,5-diyl, wherein the nitrogen atom carries H, an alkyl group having from 1 to 20 carbon atoms or an unsubstituted or substituted phenyl group; or 4-pyridyl;

$R^1, R^2, R^3, R^4$ and $R^5$ are identical or different and are each

H; an unbranched or branched alkyl group having from 1 to 12 carbon atoms, where one or more —CH$_2$— groups can be replaced by —O—; or —NR$^6{}_2$;

$R^6$ is H, an alkyl group having from 1 to 6 carbon atoms or phenyl;

a, c, d, e and g are identical or different and are 0 or 1;

b and f are identical or different and are 0, 1 or 2; with the provisos that a) the sum a+b+c+d+e+f+g is at least 5 and the group —F$_a$—D$_b$—B$_c$—A$_d$—C$_e$—E$_f$—G$_g$— contains at least 2 pyrimidine-2,5-diyl groups or that b) the sum a+b+c+d+e+f+g is at least 4 and the group —F$_a$—D$_b$—B$_c$—A$_d$—C$_e$—E$_f$—G$_g$— contains at least 3 pyrimidine-2,5-diyl groups.

7. The pyrimidine compound as claimed in claim 6, wherein the symbols and indices in the compound of the formula (I) have the following meanings:

A is pyrimidine-2,5-diyl or 1,4-phenylene;

B and C are: identical or different and are pyrimidine-2,5-diyl or 1,4-phenylene, where one or two hydrogen atoms can be replaced by radicals $R^3$; or —CH=CH—;

D and E are identical or different and are A, B, C, —B—A—C—,

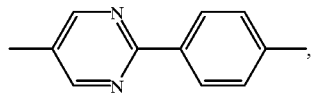

-continued

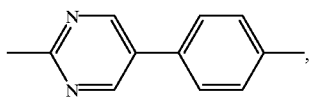

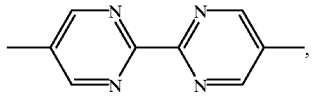

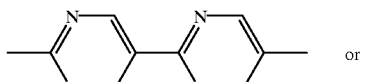 or

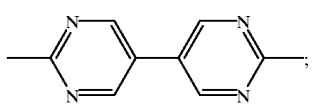

F and G are identical or different and are D or E;

$R^1$, $R^2$ and $R^3$ are identical or different and are each H; an unbranched or branched alkyl group having from 1 to 12 carbon atoms, where one —CH$_2$— group can be replaced by —O—; or —NR$^6{}_2$;

$R^6$ is H, an alkyl group having from 1 to 6 carbon atoms or phenyl;

a, c, d, e and g are identical or different and are 0 or 1;

b and f are identical or different and are 0, 1 or 2.

* * * * *